(12) United States Patent
Nett (10) Patent No.: US 12,310,768 B2
(45) Date of Patent: May 27, 2025

(54) REGION OF INTEREST COMPUTED TOMOGRAPHY IMAGING USING ONE OR MORE STATIC COLLIMATORS

(71) Applicant: GE Precision Healthcare LLC, Wauwatosa, WI (US)

(72) Inventor: Brian E. Nett, Wauwatosa, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 385 days.

(21) Appl. No.: 17/852,791

(22) Filed: Jun. 29, 2022

(65) Prior Publication Data
US 2024/0000403 A1      Jan. 4, 2024

(51) Int. Cl.
| | |
|---|---|
| A61B 6/03 | (2006.01) |
| A61B 6/00 | (2024.01) |
| A61B 6/06 | (2006.01) |
| A61B 6/40 | (2024.01) |
| A61B 6/46 | (2024.01) |
| A61N 5/10 | (2006.01) |
| A61B 6/04 | (2006.01) |

(52) U.S. Cl.
CPC ............... *A61B 6/06* (2013.01); *A61B 6/032* (2013.01); *A61B 6/035* (2013.01); *A61B 6/4035* (2013.01); *A61B 6/461* (2013.01); *A61B 6/469* (2013.01); *A61B 6/488* (2013.01); *A61B 6/5211* (2013.01); *A61B 6/547* (2013.01); *A61N 5/1049* (2013.01); *A61B 6/0407* (2013.01); *A61B 6/0487* (2020.08); *A61B 6/542* (2013.01); *A61B 6/545* (2013.01); *A61N 2005/1059* (2013.01); *A61N 2005/1061* (2013.01)

(58) Field of Classification Search
CPC ....... A61B 6/032; A61B 6/035; A61B 6/0407; A61B 6/0487; A61B 6/06; A61B 6/4035; A61B 6/461; A61B 6/469; A61B 6/488; A61B 6/5211; A61B 6/542; A61B 6/545; A61B 6/547; A61N 5/1049; A61N 2005/1059; A61N 2005/1061
See application file for complete search history.

(56) References Cited

FOREIGN PATENT DOCUMENTS

WO    WO-2010101208 A1 * 9/2010 ............. A61B 6/032

OTHER PUBLICATIONS

English translation of WO-2010101208-A1 (Year: 2010).*
H. Wang, et al. "CT Dose Minimization using Personalized Protocol Optimization and Aggressive Bowtie", 2016 SPIE Proceedings; 6 pages.

\* cited by examiner

*Primary Examiner* — Mark R Gaworecki (57) ABSTRACT

In one embodiment, a method of obtaining a computed tomography scan of a region of interest includes determining a region of interest. The region of interest is a portion of an object being scanned. The method also includes selectin an appropriate static filter of a pre-patient collimator from a plurality of pre-patient collimators and positioning the selected static filter of the pre-patient collimator in a path of an x-ray beam. The method may also include adjusting a table of the CT system to position the region of interest in the path of the region of interest.

17 Claims, 6 Drawing Sheets

REGION OF INTEREST COMPUTED TOMOGRAPHY IMAGING USING ONE OR MORE STATIC COLLIMATORS

BACKGROUND

Noninvasive imaging modalities may transmit energy in the form of radiation into an imaging subject. Based on the transmitted energy, images may be subsequently generated indicative of the structural or functional information internal to the imaging subject. In computed tomography (CT) imaging, radiation transmits from a radiation source to a detector through the imaging subject. A pre-patient collimator may be positioned in the X-ray beam path. Different anatomy of the subject may require different pre-patient collimators. For some cases, imaging of only a region of the patient is needed. While some methods exists for imaging a region of interest using dynamic collimators, a method is needed using static filters of a pre-patient collimators.

SUMMARY

In one embodiment, a method of obtaining a computed tomography scan of a region of interest includes determining a region of interest. The region of interest is a portion of an object being scanned. The method also includes selecting an appropriate static filter of a pre-patient collimator from a plurality of pre-patient collimators and positioning the selected static filter of the pre-patient collimator in a path of an x-ray beam. The method may also include adjusting a table of the CT system to position the region of interest in the path of the region of interest. Adjusting the table may include moving the table left, right, closer to the CT scanner, further from the CT scanner, up (higher) and/or down (lower). In some example embodiments, the method also includes completing an initial scan prior to determining a region of interest in order to determine how to proceed regarding a region of interest scan. In some example embodiments, the method may include determining whether the region of interest scan is appropriate for the region of interest within the object. The example method may also include finding a position of the region of interest within the object or determining a size of the region of interest. Alternatively or additionally, in some example methods, a built-in region of interest margin is added to the size and/or position of the region of interest to ensure the entire region of interest is imaged. In some examples, a user or operator may specify the position of the region of interest by inputting data in a processor of the CT system. The method may also include acquiring the region of interest scan if it is determined a region of interest scan is appropriate. In some examples, the method includes modifying a dose per view to account for off-center scan acquisitions.

An example embodiment of an imaging system described herein may include a gantry for receiving an imaging subject, a radiation source positioned in the gantry for emitting radiation exposure as an x-ray beam, a detector positioned in the gantry opposite of the radiation source, a motorized table for moving the imaging subject within the gantry, a computation device with instructions stored in a non-transient memory, a static filter of a pre-patient collimator to adjust the x-ray beam such that only a region of interest of the patient is irradiated, and a collimator controller to adjust a position of the static filter of the pre-patient collimator for a region of interest scan. The collimator controller positions the static filter of the pre-patient collimator such that the x-ray beam irradiates only a region of interest of the patient to obtain a region of interest scan. In some examples, the system may include a table controller to operate the motorized table to position the region of interest of the patient in the x-ray beam. In some examples, the system may include a processor to determine the region of interest of the patient based on a previous scan. In some examples, the system may include a camera to identify the position of the region of interest and/or to assist with positioning the object or table in the correct position. In some examples, the system may include a processor to determine whether a region of interest scan is appropriate. In some examples, the system may include a processor to determine which static filter of the pre-patient collimator to position within the path of the x-ray beam. In some examples, the system may include an image reconstructor to output an image of the region of interest based on the region of interest scan.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Figure 1:
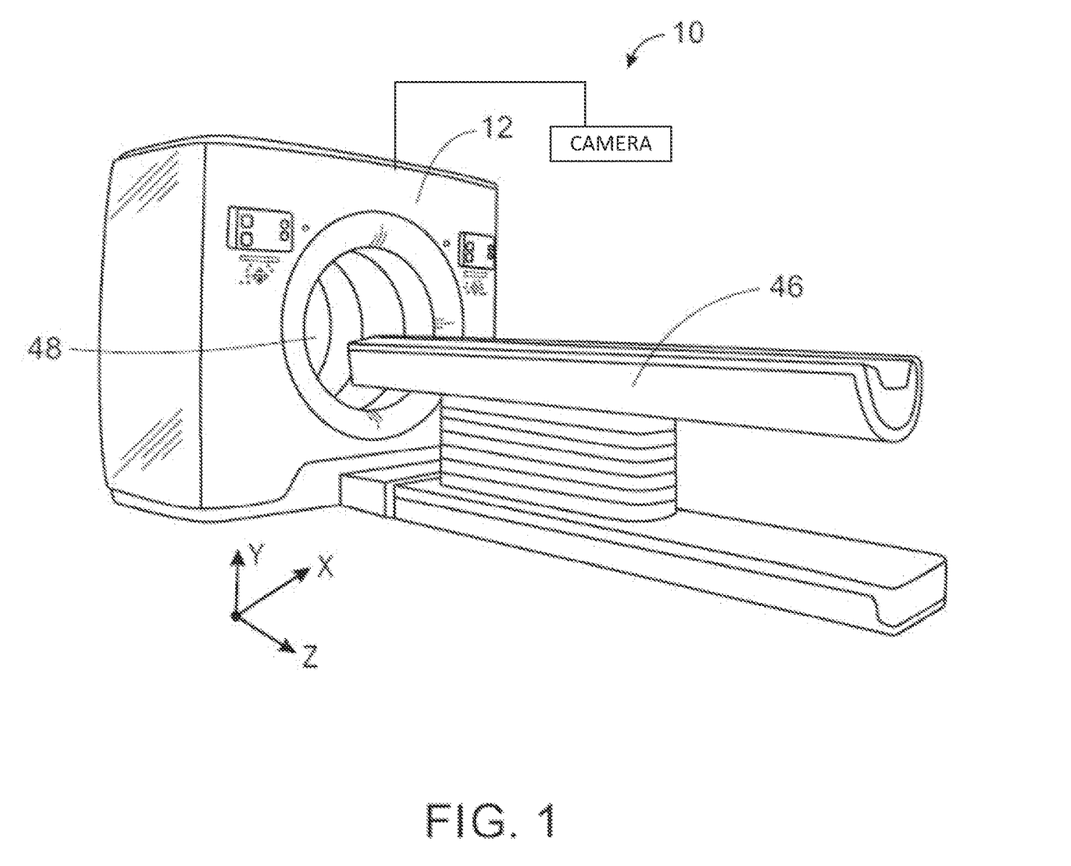
FIG. 1 shows a pictorial view of an imaging system according to an embodiment of the invention.
Figure 2:
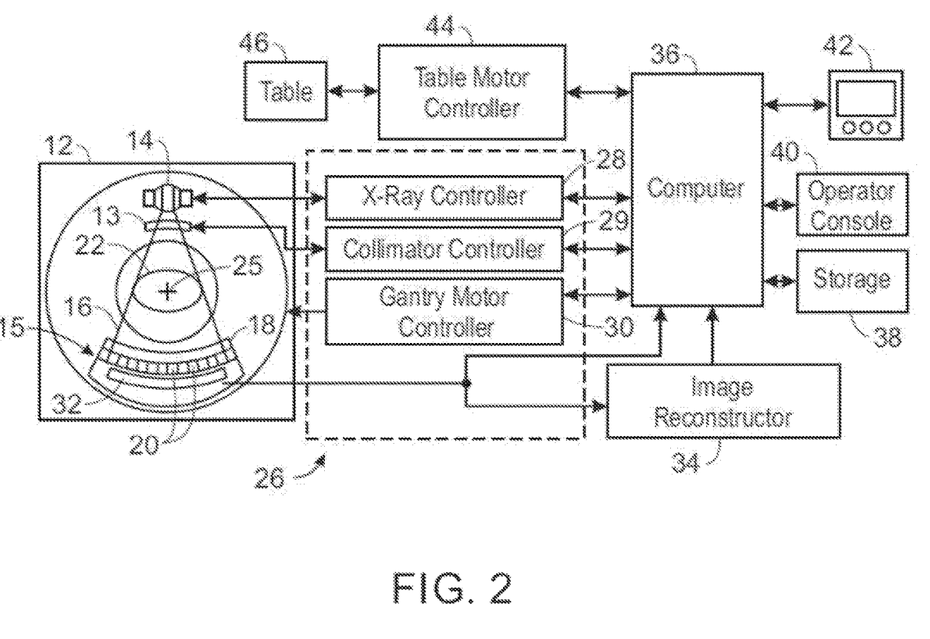
FIG. 2 shows a block schematic diagram of an exemplary imaging system according to an embodiment of the invention.
Figure 3A:
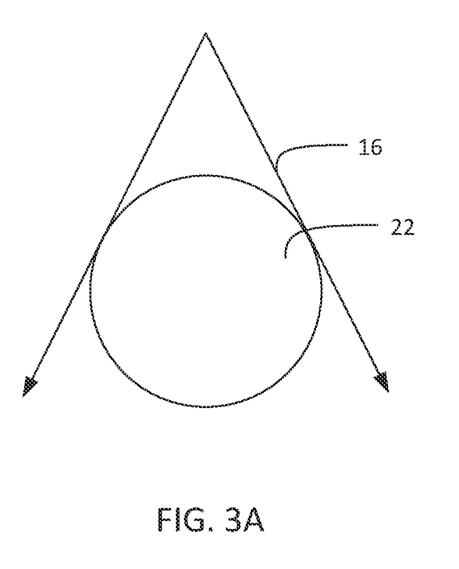
FIG. 3A depicts a traditional scan using a static filter.
Figure 3B:
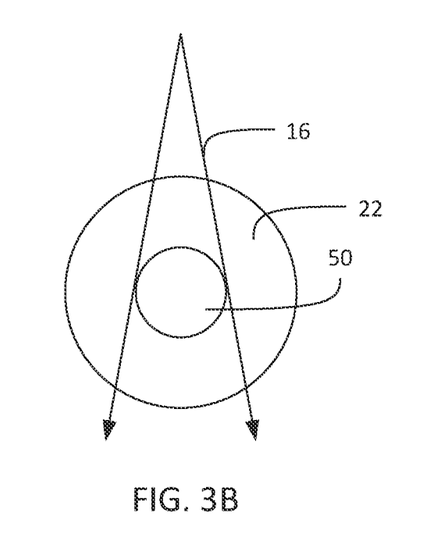
FIG. 3B depicts a region of interest scan using a static filter.
Figure 4:
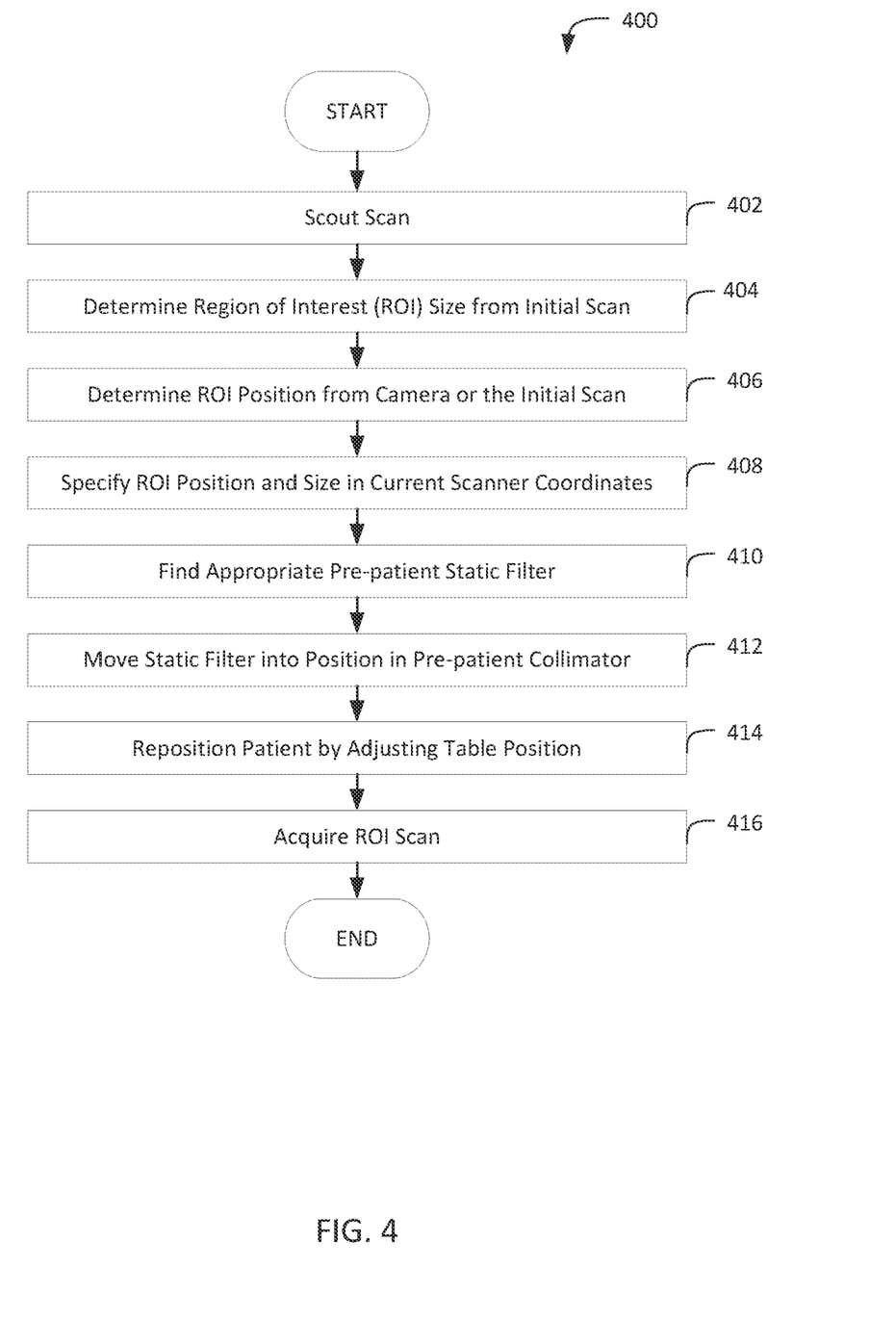
FIG. 4 shows a flow chart of an example method for obtaining a region of interest scan.
Figure 5:
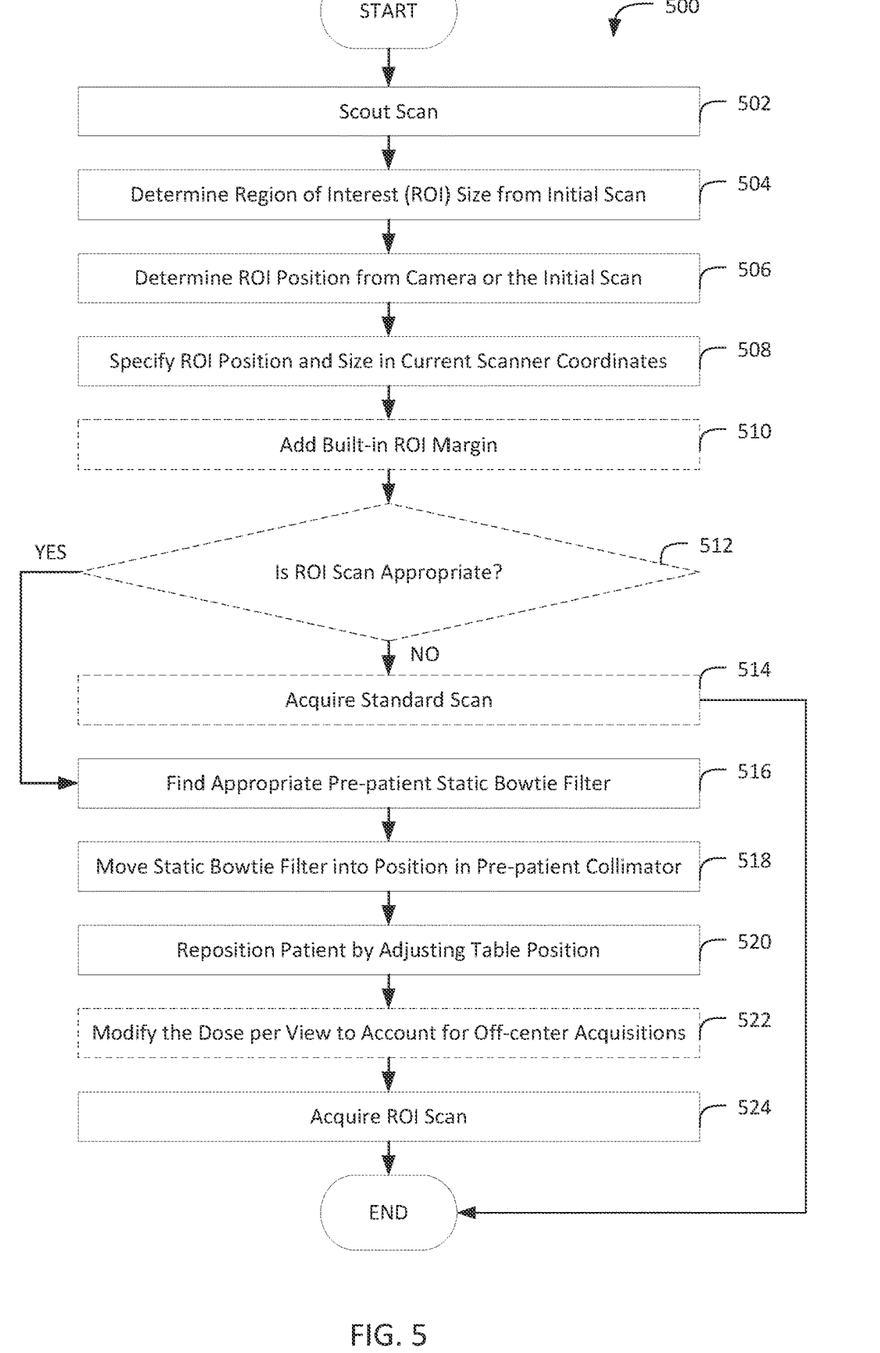
FIG. 5 shows a flow chart of another example method for obtaining a region of interest scan.

The following description relates to various example methods that may be used to obtain region of interest scans using static filter of a pre-patient collimators, and an example system which may be used to implement the example methods. In particular, systems and methods are provided for CT imaging using one or more static filters of pre-patient collimators. FIGS. 1-2 show an example embodiment of an imaging system, wherein the one or more pre-patient collimators are positioned between the radiation source and the imaging subject. Different pre-patent collimators may be selected based on the anatomy of the imaging subject being imaged and the position and/or size of the region of interest. FIGS. 3A and 3B graphically represent the reduced area that is scanned during a region of interest scan compared to a standard scan when suing the example method described herein. FIG. 4 shows an example method for obtaining a region of interest scan. FIG. 5 shows an alternative example method for obtaining a region of interest scan.

Though a CT system is described by way of example, it should be understood that the present techniques may also be useful when applied to images acquired using other imaging modalities, such as tomosynthesis, C-arm angiography, and so forth. The present discussion of a CT imaging modality is provided merely as an example of one suitable imaging modality.

Various embodiments may be implemented in connection with different types of imaging systems. For example, various embodiments may be implemented in connection with a CT imaging system in which a radiation source projects a fan- or cone-shaped beam that is collimated to lie within an x-y plane of a Cartesian coordinate system and generally referred to as an "imaging plane." The x-ray beam passes through an imaging subject, such as a patient. The beam, after being attenuated by the imaging subject, impinges upon an array of radiation detectors. The intensity of the attenuated radiation beam received at the detector array is dependent upon the attenuation of an x-ray beam by the imaging subject. Each detector element of the array produces a separate electrical signal that is a measurement of the beam intensity at the detector location. The intensity measurements from all the detectors are acquired separately to produce a transmission profile.

In third-generation CT systems, the radiation source and the detector array are rotated with a gantry within the imaging plane and around an object (such as a region of the subject) to be imaged such that the angle at which the x-ray beam intersects the imaging subject constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector. In an axial diagnostic scan, the projection data is processed to construct an image that corresponds to a two-dimensional slice taken through the imaging subject. A scout scan (also referred herein as localizer scan) provides a projection view along a longitudinal axis of the imaging subject and generally provides aggregations each including internal structures of the subject. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on a display.

FIG. 1 illustrates an exemplary computed tomography (CT) imaging system 10 and FIG. 2 depicts an example block diagram of the exemplary imaging system according to an embodiment of the invention. The CT imaging system includes a gantry 12. The gantry 12 has an X-ray source 14 that generates and projects a beam of X-rays 16 toward a detector assembly 15 on the opposite side of the gantry 12. The X-ray source 14 projects the beam of X-rays 16 through a pre-patient collimator assembly 13 that determines the size and shape of the beam of X-rays 16 using, for example, one or more filters. The detector assembly 15 includes a collimator assembly 18 (a post-patient collimator assembly), a plurality of detector modules 20 (e.g., detector elements or sensors), and data acquisition systems (DAS) 32. The plurality of detector modules 20 detect the projected X-rays that pass through a subject or object 22 being imaged, and DAS 32 converts the data into digital signals for subsequent processing. Each detector module 20 in a conventional system produces an analog electrical signal that represents the intensity of an incident X-ray beam and hence the attenuated beam as it passes through the subject or object 22. During a scan to acquire X-ray projection data, gantry 12 and the components mounted thereon rotate about a center of rotation 25 (e.g., isocenter) so as to collect attenuation data from a plurality of view angles relative to the imaged volume.

Rotation of gantry 12 and the operation of X-ray source 14 are governed by a control system 26 of CT imaging system 10. Control system 26 includes an X-ray controller 28 that provides power and timing signals to an X-ray source 14, a collimator controller 29 that controls a length and a width of an aperture of the pre-patient collimator 13 (and, thus, the size and shape of the beam of X-rays (e.g., x-ray beam) 16), and a gantry motor controller 30 that controls the rotational speed and position of gantry 12. An image reconstructor 34 receives sampled and digitized X-ray data from DAS 32 and performs high-speed image reconstruction. The reconstructed image is applied as an input to a computer 36, which stores the image in a storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, collimator controller 29, and gantry motor controller 30. In addition, computer 36 operates a table motor controller 44, which controls a motorized table 46 to position subject 22 and gantry 12. Particularly, table 46 moves portions of subject 22 through a gantry opening or bore 48. One or more cameras 11 may also be used to ensure the patient or a Region of Interest of the patient is positioned properly positioned in the path of the X-rays 16.

In accordance with aspects of the present disclosure, the imaging system 10 is configured to perform automatic exposure control responsive to user input. Exposure control may be achieved using one or more filter that may be mounted within gantry 12 between x-ray source 14 and the subject 22. The filter assemblies may travel in and out of the beam 16 in the z-direction while the beam 16 is substantially in the y-direction.

FIG. 3A depicts an X-ray beam path 16 during a traditional scan. The X-ray beam path 16 is typically broad enough to encompass the entire subject 22 to be scanned. For example, if a patient is being scanned, the X-ray beam path 16 is wide enough that the entire width of the patient is within the edges of the X-ray beam path 16. Thus, the full body of the patient can be imaged using a traditional scan. However, since the entire width of the patient is in the X-ray beam path 16, the entire width of the patient is being exposed to radiation, which increases the patient's dosage. While traditional, whole patient scans are necessary in some cases, such as for scout or initial scans to determine a region of interest 50 or an initial diagnosis, the exposure to the X-ray beams 16 can be reduced for a more targeted region of interest scan after the operator has determined a target area or organ to be imaged.

FIG. 3B depicts an example X-ray beam path 16 during a targeted or region of interest scan. In this example, a region of interest 50 has been identified by the operator, for example, as part of a longitudinal study to track a region of interest 50 in a subject 22 over time. A filter or pre-patient collimator has been positioned in the X-ray beam path 16 to narrow the X-ray beam path 16 that reaches the subject 22. Specifically, the narrowed X-ray beam path is wide enough to encompass the region of interest 50, but does not pass through the entire width of the patient, thus reducing the radiation dose received by the patient. For example, if the operator determines that the heart is the region of interest 50 in a subject 22, a pre-patient collimator 13 may be used that narrows the X-ray beam 16 to the width of the heart, rather the X-ray beam 16 extending across the entire width of the patient's chest. The same area is covered by each region of interest scan in the example longitudinal study so that the images can be compared over the duration of a treatment time. Region of interest scans may be especially desirable for longitudinal studies to reduce the dose on the patient during the treatment time, when compared to using only traditional scans during the treatment time.

In examples where the region of interest 50 is positioned approximately in the center of a subject 22, or where the region of interest 50 can be moved (e.g., by repositioning the table) so that the region of interest 50 is approximately at the center 25 of the gantry 12, a bowtie-shaped pre-patient collimator 13 (i.e., bowtie filter) may be used as the pre-patient collimator that narrows the X-ray beam 16. Alternatively, when the region of interest 50 is offset from the center 25 of the gantry 12, an asymmetric bowtie filter may be used to focus and narrow the X-ray beam 16 on the off-center region of interest 50. In an alternative example, a pre-patient collimator 13 used during a traditional scan may not produce an X-ray beam 16 with a wide enough path for a region of interest 50 (specifically for larger patients), so a flat pre-patient collimator may be used instead to widen the X-ray beam 16 for a region of interest 50.

FIG. 4 shows a flow chart of an example method 400 for obtaining a region of interest scan. The method 400 of obtaining a region of interest scan described herein includes first obtaining an initial scan (step 402). The initial scan may be a scout scan, a low-dose scan, a previous scan, or a traditional scan taken while a patient is positioned on the table so the region of interest 50 at the time of the scan can be identified. The initial scan may produce a 2D or a 3D image. A size of the region of interest 50 can be determined based on the scout scan (step 404). In some examples, the size of the region of interest 50 is determined by an operator reviewing the image from the scout scan and determining the size of the region of interest 50 based on the image. A position of the region of interest in the initial is also determined (step 406). The position of the region of interest 50 may be defined as a center or approximate center of the region of interest 50, while the size determined in step 404 refers to, for example, a radius or outer bounds of the region of interest 50. The position of the region of interest can be determined using the image from the scout scan, observing the position of the patient on the table, and/or the relative position of the table to the gantry. In some examples, cameras may help define a coordinate system to determine where the patient is positioned, and thus determine the position of the region of interest 50 within the patient. For example, cameras can be used to define a surface of the patient anatomy and register the surface defined by the cameras to a surface of the patient anatomy determined based using the image obtained during the initial scan. Additionally, other previous scans (prior to the initial scan) may also be used to help determine the position and/or size of the region of interest, or may be used as a baseline for a comparison during a course of treatment. If the previous scan(s) includes an annotation referencing the region of interest 50, the data from the previous scan may be registered against the new region of interest scan to match the coordinates of the two scans to enable an accurate comparison of the region of interest 50 in each scan. The position and size of the region of interest is then specified (step 408) in the current scanner coordinates. In some examples, specifying the region of interest 50 includes providing coordinates and/or location and size information to the computer to prepare for image acquisition.

The method 400 continues by determining an appropriate filter of a pre-patient collimator that will best focus the X-ray beam 16 on the region of interest (step 410). In some examples, the best static filter for a pre-patient collimator is selected from a plurality of available filters, and may be a bowtie shape, an asymmetrical bowtie shape, or flat. The best filter is moved, if necessary, into position in the pre-patient collimator between the X-ray beam generator and the patient (step 412).

The table is repositioned to reposition the patient (step 414), for example, to align the center of the region of interest with the center of rotation for the gantry as closely as possible. In some examples, such as when an asymmetric bowtie-shaped filter is used, the position of interest may also be off-center from the center of rotation for the gantry. The table may be moved left or right (e.g., lateral position), up or down (e.g., table height), or longitudinally within the gantry in order to position the center of the region of interest appropriately for the region of interest scan. Finally, the region of interest scan is acquired (step 416). After the region of interest scan is complete, method 400 is complete.

FIG. 5 shows a flow chart of an example method 500 for obtaining a region of interest scan. The method 500 of obtaining a region of interest scan described herein includes first obtaining an initial scan (step 502). The initial scan may be a scout scan, a low-dose scan, a previous scan, or a traditional scan taken while a patient is positioned on the table so the region of interest 50 at the time of the scan can be identified. The initial scan may produce a 2D or a 3D image. A size of the region of interest 50 can be determined based on the scout scan (step 504). In some examples, the size of the region of interest 50 is determined by an operator reviewing the image from the scout scan and determining the size of the region of interest 50 based on the image. A position of the region of interest in the initial is also determined (step 506). The position of the region of interest 50 may be defined as a center or approximate center of the region of interest 50, while the size determined in step 504 refers to, for example, a radius or outer bounds of the region of interest 50. The position of the region of interest can be determined using the image from the scout scan, observing the position of the patient on the table, and/or the relative position of the table to the gantry. In some examples, cameras 11 may help define a coordinate system to determine where the patient is positioned, and thus determine the position of the region of interest 50 within the patient. For example, cameras 11 can be used to define a surface of the patient anatomy and register the surface defined by the cameras 11 to a surface of the patient anatomy determined based using the image obtained during the initial scan. Additionally, other previous scans (prior to the initial scan) may also be used to help determine the position and/or size of the region of interest, or may be used as a baseline for a comparison during a course of treatment. If the previous scan(s) includes an annotation referencing the region of interest 50, the data from the previous scan may be registered against the new region of interest scan to match the coordinates of the two scans to enable an accurate comparison of the region of interest 50 in each scan. The position and size of the region of interest is then specified (step 508) in the current scanner coordinates. In some examples, specifying the region of interest 50 includes providing coordinates and/or location and size information to the computer to prepare for image acquisition.

In some examples, a built-in region of interest margin is added to the size of the region of interest 50 (step 510). In such examples, the built-in margin ensures that the entire region of interest 50 is imaged by increasing the determined size of the region of interest by a pre-determined factor or percentage (e.g., 5%) to account for any positioning or measuring errors. In some examples, an operator or processor may determine whether the ROI scan is appropriate (step 512) by determining if the region of interest can be appropriately positioned (e.g., substantially centered within the gantry). In some examples, the position or size of the region of interest would not result in an adequate image being captured, and a traditional scan would be more favorable. If a region of interest scan is not appropriate, the method 500 is complete, but a traditional scan may be acquired instead (step 514). If a region of interest scan is appropriate, the method 500 continues by determining an appropriate filter of a pre-patient collimator that will best focus the X-ray beam 16 on the region of interest (step 516). In some examples, the best static filter for a pre-patient collimator is selected from a plurality of available filters, and may be a bowtie shape, an asymmetrical bowtie shape, or flat. The best filter is moved, if necessary, into position in the pre-patient collimator between the X-ray beam generator and the patient (step 518).

The table is repositioned to reposition the patient (step 520), for example, to align the center of the region of interest with the center of rotation for the gantry as closely as possible. In some examples, such as when an asymmetric bowtie-shaped filter is used, the position of interest may also be off-center from the center of rotation for the gantry. The table may be moved left or right (e.g., lateral position), up or down (e.g., table height), or longitudinally within the gantry in order to position the center of the region of interest appropriately for the region of interest scan. In some examples, the dose per view of the scan may be modified to account for off-center acquisitions (step 522). The dose can be modified by changing the input parameters and/or by modifying a table created by an Automated Exposure Control (AEC) on a per patient basis. Modifying the dose per view in this way results in a lower dose than a standard scan. Finally, the region of interest scan is acquired (step 524). After the region of interest scan is complete, method 500 is complete.

Figure 6:
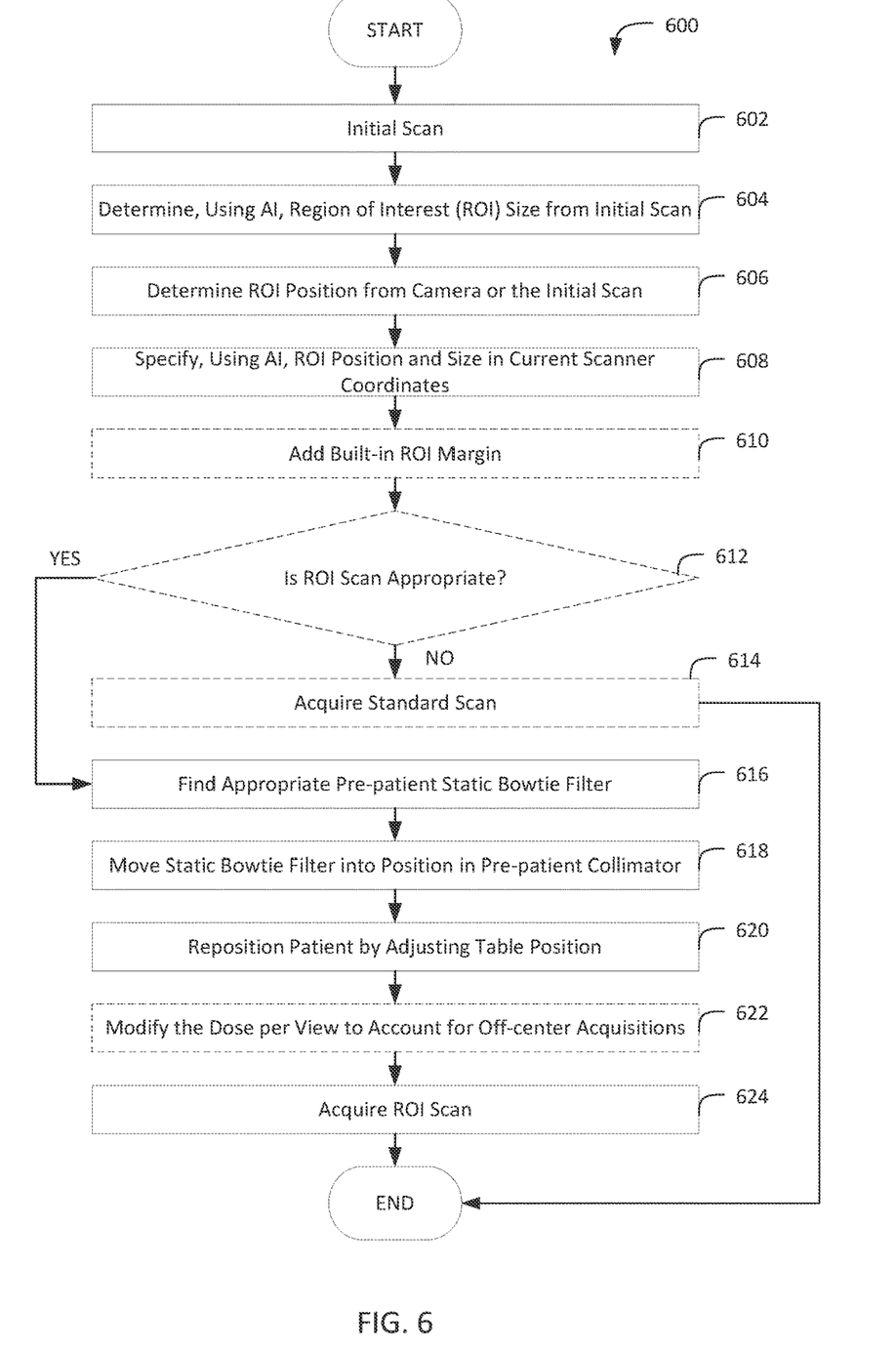
FIG. 6 shows a flow chart of an alternative example method for obtaining a region of interest scan.

FIG. 6 shows a flow chart of an example method 600 for obtaining a region of interest scan. The method 600 of obtaining a region of interest scan described herein includes first obtaining an initial scan (step 602). The initial scan may be a scout scan or a traditional scan taken while a patient is positioned on the table so the region of interest 50 at the time of the scan can be identified. The initial scan may produce a 2D or a 3D image. A size of the region of interest 50 can be determined based on the scout scan (step 604). In some examples, the size of the region of interest 50 is determined using Artificial Intelligence (AI) evaluating the image from the scout scan to determine the size of the region of interest 50. A position of the region of interest in the initial scan is also determined (step 606) using AI. The position of the region of interest 50 may be defined as a center or approximate center of the region of interest 50, while the size determined in step 604 refers to, for example, a radius or outer bounds of the region of interest 50. The position of the region of interest can be determined using the image from the scout scan and using cameras 11 to determine the position of the patient on the table and/or the relative position of the table to the gantry. In some examples, AI can use the images from the cameras 11 to define a coordinate system and determine where the patient is positioned. For example, cameras 11 can be used to define a surface of the patient anatomy and register the surface defined by the cameras 11 to a surface of the patient anatomy determined based using the image obtained during the initial scan and/or previous scans. The position and size of the region of interest is then specified (step 608) in the current scanner coordinates. In some examples, specifying the region of interest 50 includes AI providing coordinates and/or location and size information to the computer as an input to prepare for image acquisition.

In some examples, a built-in region of interest margin is added to the size of the region of interest 50 (step 610). In such examples, the built-in margin ensures that the entire region of interest 50 is imaged by increasing the determined size of the region of interest by a pre-determined factor or percentage (e.g., 5%) to account for any positioning or measuring errors. In some examples, an operator or processor may determine whether the ROI scan is appropriate (step 612) by determining if the region of interest can be appropriately positioned (e.g., substantially centered within the gantry). In some examples, the position or size of the region of interest would not result in an adequate image being captured, and a traditional scan would be more favorable. If a region of interest scan is not appropriate, the method 600 is complete, but a traditional scan may be acquired instead (step 614). If a region of interest scan is appropriate, method 600 continues by determining an appropriate filter of a pre-patient collimator that will best focus the X-ray beam 16 on the region of interest (step 616). In some examples, the best static filter for a pre-patient collimator is selected from a plurality of available filters, and may be a bowtie shape, an asymmetrical bowtie shape, or flat. The best filter is moved, if necessary, into position in the pre-patient collimator between the X-ray beam generator and the patient (step 618).

The table is repositioned to reposition the patient (step 620), for example, to align the center of the region of interest with the center of rotation for the gantry as closely as possible. In some examples, such as when an asymmetric bowtie-shaped filter is used, the position of interest may also be off-center from the center of rotation for the gantry. The table may be moved left or right, up or down, or longitudinally within the gantry in order to position the center of the region of interest appropriately for the region of interest scan. In some examples, the dose per view of the scan may be modified to account for off-center acquisitions (step 622). The dose can be modified by changing the input parameters and/or by modifying a table created by an Automated Exposure Control (AEC) on a per patient basis. Modifying the dose per view in this way results in a lower dose than a standard scan. Finally, the region of interest scan is acquired (step 624). After the region of interest scan is complete, method 600 is complete.

The example methods 400, 500, and 600 may, in some cases, be combined. For example, a step done manually or by an operator in method 400 or 500 may be combined with steps done using AI from method 600. Furthermore, some steps may be completed simultaneously or in a different order. For example, the table may be moved (steps 414, 520, 620) may instead be completed prior to or simultaneously with moving the pre-patient collimator (steps 412, 518, 618).

FIGS. 1-3B show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of obtaining a computed tomography scan of a region of interest, the method comprising:
   determining a region of interest, wherein the region of interest is a portion of an object being scanned;
   adding a built-in region of interest margin to a size of the region of interest;
   selecting an appropriate static filter of a pre-patient collimator from a plurality of pre-patient collimators;
   positioning the selected static filter of the pre-patient collimator in a path of an x-ray beam; and
   adjusting a table to position the region of interest in the path of the region of interest.

2. The method of claim 1, further comprising, prior to determining a region of interest, completing an initial scan, wherein the region of interest is determined based on the initial scan.

3. The method of claim 1, further comprising finding a position of the region of interest.

4. The method of claim 3, further comprising specifying the position of the region of interest.

5. The method of claim 1, further comprising determining whether a region of interest scan is appropriate.

6. The method of claim 1, wherein adjusting the position of the table includes adjusting a table height.

7. The method of claim 1, wherein adjusting the position of the table includes adjusting a lateral position of the table.

8. The method of claim 1, further including acquiring the scan of the region of interest.

9. The method of claim 1, further including modifying a dose per view to account for off-center scan acquisitions.

10. The method of claim 1, further comprising determining the size of the region of interest.

11. The method of claim 10, wherein the static filter is selected based on the size of the region of interest.

12. An imaging system, comprising:
    a gantry for receiving an imaging subject;
    a radiation source positioned in the gantry for emitting radiation exposure as an x-ray beam;
    a detector positioned on the opposite of the gantry relative to the radiation source;
    a motorized table for moving the imaging subject within the gantry;

a static filter of a pre-patient collimator, the static filter of the pre-patient collimator to adjust the x-ray beam such that only a region of interest of the patient is irradiated;

a collimator controller to adjust a position of the static filter and the pre-patient collimator for a region of interest scan, wherein the collimator controller positions the static filter and the pre-patient collimator such that the x-ray beam irradiates only a region of interest of the patient to obtain a region of interest scan; and a camera to identify the position of the region of interest.

13. The imaging system of claim 12, further including a table controller to operate the motorized table to position the region of interest of the patient in the x-ray beam.

14. The imaging system of claim 12, further including a processor to determine the region of interest of the patient based on a previous scan.

15. The imaging system of claim 12, further including a processor to determine whether a region of interest scan is appropriate.

16. The imaging system of claim 12, further including a processor to determine which static filter of the pre-patient collimator to position within a path of the x-ray beam.

17. The imaging system of claim 12, further including an image reconstructor to output an image of the region of interest based on the region of interest scan.

* * * * *